United States Patent [19]

Matyasi et al.

[11] 4,225,639

[45] Sep. 30, 1980

[54] PROCESS FOR PREPARING ALUMINA BEING SUITABLE FOR LAYER CHROMATOGRAPHY

[75] Inventors: József Mátyási, Almásfüzitó-felső; Béla Kökeny; László Zsembery, both of Almásfüzitó; György Kaptay; Sándor Németh, both of Almásfüzitö-felsö, all of Hungary

[73] Assignee: Magyar Aluminiumipari Troszt, Budapest, Hungary

[21] Appl. No.: 49,653

[22] Filed: Jun. 19, 1979

[30] Foreign Application Priority Data

Jun. 26, 1978 [HU] Hungary .............................. AA 900

[51] Int. Cl.² .......................... C01F 7/02; B01D 15/08
[52] U.S. Cl. ................................ 427/372.2; 423/625; 423/630; 210/198C
[58] Field of Search ............... 423/127, 630, 625, 628; 427/372 R; 210/198 C

[56] References Cited

U.S. PATENT DOCUMENTS

| | | | |
|---|---|---|---|
| 2,247,624 | 7/1941 | Wall | 423/630 |
| 2,894,915 | 7/1959 | Keith | 423/628 |
| 2,898,307 | 8/1959 | Keith | 423/628 |
| 3,539,468 | 11/1970 | Wright | 423/127 |
| 3,542,588 | 11/1970 | Heidbrink | 427/372 R |
| 3,726,405 | 4/1973 | Engelbrecht | 210/198 C |

OTHER PUBLICATIONS

Frey, H. "Chromatographic Separations on Ultrathin Silica Gel and Aluminum Oxide Layers" in *Chemical Abstracts* vol. 77, 1972, #96524n.

*Primary Examiner*—Brian E. Hearn
*Attorney, Agent, or Firm*—Young & Thompson

[57] ABSTRACT

The invention relates to a process for preparing alumina being suitable for layer chromatography.

The alumina suitable for layer chromatography is prepared in accordance with the invention in such a manner that an aluminium trinydroxyde containing 34 to 37% by weight of bayerite, 3 to 5% by weight of pseudoboehmite and 60 to 62% by weight of amorphous aluminium trihydroxide is heated at 300° C. to 400° C. for 2 to 4 hours.

The activated alumina thus produced is snow-white, has a large specific surface and its average grain size is within the range between 8 and 20 μm.

The product complies with the requirements of layer chromatographical technique.

7 Claims, No Drawings

PROCESS FOR PREPARING ALUMINA BEING SUITABLE FOR LAYER CHROMATOGRAPHY

The invention relates to a new process for the preparation of alumina being suitable for performing layer chromatography.

It is of utmost importance that the alumina powder used for layer chromatographical purposes should well adhere to the plate in order to prevent its separation from the plate in course of applying the solution or developing. The problem has been tried to solve by using different additives, such as calcium sulphate and polyvinyl alcohol or by gluing.

In accordance with a patent of the company Kodak Pathe the adsorbent is applied onto a synthetic plate known under the name Mylar in a mixture with a synthetic powder of polycarbonate known as Makrolon S and suspended in methyl glycol. After having been dried, the plates are cut to the proper size (French Pat. No. 1,370,780).

In accordance with the Saithola process, the alumina powder suitable for chromatography and available in the market is glued in a mixture with polyvinyl alcohol to the synthetic plate made of polyethylene terephtalate (Journal of Chromatography, volume 30/1967/, pages 493–501).

The said processes have the disadvantage that no coherent alumina layer suitable for layer chromatographical development can be achieved, and even at the most careful appliance capillaries occur.

Hermanek and Sosnova simply strewed the alumina powder suitable for chromatography, available in commerce onto the glass plate and smoothed by means of a glass rod. (Izv. Akad. Nauk Kazah, S.S.R. Ser. Chim., Vol. 22/1972/3, page 29.)

By using this method plates being utmost sensitive to damages could be obtained.

The alumina suitable for chromatographical purposes sold in the commerce under the names Merck G Typ E and Fluka D 5 contain 10% and 5% calcium sulphate, additives, respectively. The layers prepared of them rather tend to damaging and do not properly adhere to the plate.

The products of the same companies, known under the names Merck H and Fluka Do, which do not contain binding materials, are showing even worse adhesive properties (British Pat. No. 1,054,576).

Layer chromatographical alumina is mostly used for analytical purposes, for the separation of the mixtures of organic and inorganic compounds, to qualitative and quantitative analysis in chemistry.

The adsorbent layer of layer chromatographical plates have to adhere onto the plate in a fairly stable manner in order to be able to perform analytical tests. It is of utmost importance that it should not crack in course of drying, since the cracked layers prevent the uniform absorption of the solvent during the development, thus rendering the analytical determination inexact.

For layer chromatographical purposes mostly the following adsorbents are used: silica gel (Kieselgel), alumina, siliceous earth (Kieselgur), cellulose powder.

Compounds of different functional groups may be separated on certain types of adsorbents. Alumina is especially suitable for the separation of neutral organic substances or those of basic character, such as aromatic hydrocarbons, terpenes, sesquiterpenes, aliphatic alcohols, aliphatic amines, imidazols, volatile oils, glycerides, alkaloides. It can be used for the separation of inorganic substances, such as the metal combinations Cu-Co-Ni, Mo-V-W, Re-Mo-W, Rh-Ru-Pt and Ir-Cu as well.

The alumina used in the layer chromatography should be snow-white, it should have a great specific surface and should be substantially free of impurities. The fine grain size is imperative, i.e. the alumina must not contain grains greater than 63 $\mu$m, and it should have an average grain size from 8 to 20 $\mu$m.

The snow-white colour is necessary for the evaluation of the chromatograms. After having performed developing, the compounds thus separated will appear in form of coloured spots; on a coloured alumina it is impossible to determine either the boundary, or the area of the spots being of decisive importance at quantitative determinations.

The specific surface has a bearing on the adsorptive properties of the layer, i.e. the rate of separation of the compounds.

The impurities contained in the alumina may exert an influence on separation (dissolution) in course of chromatography so the alumina used for layer chromatography most not contain colloidal ferric trioxide, titanium dioxide and sodium salts of the humic acid.

When applying the layers, the grain size plays an important role, since coarse-grained material precipitates in the spreading machine and prevents formation of a uniform layer, the plate becomes "striped". Such a plate is unsuitable for development as the solvent is adsorbed unevenly.

The aim of the invention is the preparation of alumina suitable for layer chromatography, by means of a simple technology. The object of the invention is the preparation of alumina that has a great specific surface, a snow-white colour and a grain size complying with the requirements previously described, adheres well to the plate and can be adjusted to optional activity.

We have found that alumina suitable for layer chromatography showing optimal features can be produced by heating aluminum trihydroxide—having the mineralogical composition detailed beneath—at about 350° C., for about three hours:

34–37% by weight of bayerite
3–5% by weight of pseudoboehmite
60–62% by weight of amorphous aluminium trihydroxide.

Accordingly, in sense of the invention aluminium trihydroxide containing 34–37% by weight of bayerite, 3–5% by weight of pseudoboehmite and 60–62% by weight of amorphous aluminium trihydroxide is heated at 300° C. to 400° C. for 2 to 4 hours.

Preferably an aluminium trihydroxide is used, that has an average grain size from 8 to 20 $\mu$m and contains grains with a size less than 63 $\mu$m.

In order to comply with the high requirements of purity, preferably a starting material is used which does not contain iron(III)oxide, titanium oxide or sodium salts of humic acid. The starting material can be produced by means of any known technology suitable for producing aluminium trihydroxide of the desired mineralogical composition, having the grain size described before.

We have found that aluminium trihydroxide as starting material can be advantageously produced by precipitation with carbon dioxide from a sodium aluminate solution containing 80 to 90 g/l alumina, performing the process at a temperature of 20° C. to 40° C. The caustic molar ratio of the sodium aluminate solution amounts preferably to 1.8 to 1.9 (Na₂O moles/Al₂O₃ moles). By using this method, the starting material, i.e. aluminium trihydroxide, can be produced as follows:

8 liters of sodium aluminate solution containing 80 g/l alumina and having a caustic molar ratio of 1.8 and being free of colloidal iron(III)oxyde, titanium dioxide and sodium salts of humic acid is filled at a temperature of 30° C., into an autoclave provided with an agitator, a perforated pipe for the introduction of carbon dioxide, a manometer and a thermometer, furthermore with an adjustable valve for discharging the carbon dioxide.

After having closed the autoclave, the solution is mixed and carbon dioxide gas is introduced.

The precipitation of aluminium trihydroxide is continued for 90 minutes at 30° C. to 40° C. When the separation is finished, the suspension is separated from the mother liquor by filtration and the filter cake is washed to neutral with water of the temperature of 30° C. to 40° C. The filter cake thus washed is dried at 110° C.

After having performed separation, the composition of the aluminium trihydroxide obtained is as follows:
- 34 to 37% by weight of bayerite,
- 3 to 5% by weight of pseudoboehmite
- 60 to 62% by weight of amorphous aluminium trihydroxide.

The thus obtained aluminium trihydroxide is heated according to the invention at a temperature of 300° C. to 400° C. The preferable temperature is 350° C. The heating period is 2 to 4 hours, preferably 3 hours.

By using the process according to the invention, a snow-white activated alumina may be obtained, complying with the strict requirements of the layer chromatographical technique. The product has an average grain size of 8 to 20 μm, and a great specific surface. The alumina thus obtained can be used for the preparation of a layer chromatographical plate in the usual manner.

Expediently, the activated product is suspended in water and after having applied onto the plate it is dried at a temperature of 30° to 100° C. for 1 to 3 hours. The drying is performed preferably at a temperature of 50° C.

The layer chromatography plates can be prepared for instance in the way as follows. To 100 g. of activated alumina 110 to 120 ml of distilled water is added. By using an usual spreading device crack-free and uniform layers in a thickness of 200 to 1800 μm can be applied onto the glass plate; the plates dried at 30° C. to 100° C. show an activity within the range between II and V.

The correlation between drying and activity is shown in table 1.

TABLE 1

| Property | Correlation between drying and activity | | | | |
|---|---|---|---|---|---|
| | Drying | | | | |
| | 30° C./8 h | 50° C./1 h | 50° C./2 h | 100° C./1 h | 100° C./2 h |
| Temperature of development °C. | 25 | 25 | 25 | 25 | 25 |
| Duration of development minutes | 60 | 63 | 59 | 64 | 58 |
| Rf 1 | 0.98 | 0.95 | 0.63 | 0.55 | 0.45 |
| Rf 2 | 0.86 | 0.66 | 0.35 | 0.23 | 0.14 |
| Rf 3 | 0.67 | 0.37 | 0.17 | 0.07 | 0.03 |
| Rf 4 | 0.36 | 0.15 | 0.07 | 0.02 | 0 |
| Rf 5 | 0.10 | 0.04 | 0.02 | 0 | 0 |
| Activity | IV-V | III-IV | II-III | II-III | below II |

The activity has been characterized by using the Brockmann-Schodder method, according to which solutions are prepared in 50 ml carbon tetrachloride from 20 ml each of the following colouring substances:
1. azobenzene
2. p-methoxyazobenezene
3. Sudan yellow
4. Sudan red
5. p-aminoazobenzene.

20 microlitres of the solutions have been applied onto the plate and developed in carbon tetrachloride.

The alumina of the activity II, III, IV and V, well suitable for layer chromatographical tests is produced by drying at a temperature of 30° C. to 100° C. for 1 to 8 hours (Table 2).

TABLE 2

| Activity | temperature (° C.) | duration (hours) |
|---|---|---|
| | of drying | |
| II | 100 | 1.5 |
| III | 50 | 2.0 |
| | 100 | 1.0 |
| IV | 50 | 1.5 |
| V | 50 | 1.0 |
| | 30 | 8.0 |

The process according to the invention should be illustrated by means of the following example.

Aluminium trihydroxide containing grains less than 63 μm, with a mineralogical composition of
- 35% by weight of bayerite
- 4% by weight of pseudoboehmite
- 61% by weight of amorphous aluminium trihydroxide, is used as a starting material. This material is heated to 350° C. and kept at this temperature for 3 hours. The product thus obtained is a snow-white alumina having an average grain size of 15 μm. An aqueous suspension is prepared from the activated substance by adding 110 to 120 ml of distilled water to 100 g of alumina. The suspension is applied onto a glass plate by the aid of a spreading device. The plates are allowed to stand for a short period (1 to 2 hours) and in order to reach activity values in the range between II and V they are dried under the following circumstances:

| Values of activity | temperature (°C.) | duration (hours) |
|---|---|---|
| | of drying | |
| II | 100 | 1.5 |
| III | 100 | 1.0 or |
| | 50 | 2.0 |
| IV | 50 | 1.5 |
| V | 50 | 1.0 or |
| | 30 | 8.0 |

What we claim is:

1. Process for producing alumina being suitable for layer chromatography, characterized in that an aluminium trihydroxide containing 34 to 37% by weight of bayerite, 3 to 5% by weight of pseudoboehmite and 60 to 62% by weight of amorphous aluminium trihydroxide is heated at 300° C. to 400° C. for 2 to 4 hours.

2. Process as claimed in claim 1, characterized in that the average grain size of the starting material is between 8 and 20 μm.

3. Process as claimed in claim 1, characterized in that the heating is performed at a temperature of 350° C. for 3 hours.

4. Process as claimed in claim 1, characterized in that the starting material is free of colloidal iron(III)oxide, titanium oxide and sodium salts of humic acid.

5. Process as claimed in any of the claims 1, 2, 3 or 4, characterized in that after having been suspended and applied onto the plate the activated material is dried for 1 to 3 hours at a temperature of 30° C. to 100° C.

6. Process as claimed in claim 5, characterized in that drying is performed at a temperature of 50° C.

7. Process as claimed in claim 1, characterized in that the aluminium trihydroxide, a starting material, is prepared by carbon dioxide precipitation at a temperature of 20° C. to 40° C. from a sodium aluminate solution containing 80 to 90 g/l alumina.

* * * * *